(12) United States Patent
Liang et al.

(10) Patent No.: US 12,203,899 B1
(45) Date of Patent: Jan. 21, 2025

(54) SAMPLE MOUNTING DEVICE FOR A DIRECT TENSILE TEST OF ROCK MASS

(71) Applicants: Institute of Geology and Geophysics, CAS, Beijing (CN); Yunnan Dianzhong Water Diversion Engineering Co., Kunming (CN)

(72) Inventors: Ning Liang, Beijing (CN); Jing Xu, Beijing (CN); Shufang Li, Beijing (CN); Tao Wang, Beijing (CN); Shengwen Qi, Beijing (CN); Jianing Cong, Beijing (CN); Bowen Zheng, Beijing (CN); Songfeng Guo, Beijing (CN); Xin Wang, Beijing (CN); Lina Ma, Beijing (CN); Shuaihua Song, Beijing (CN); Yongchao Li, Beijing (CN); Yu Zou, Beijing (CN); Xiaokun Hou, Beijing (CN); Zan Wang, Beijing (CN); Weiwei Zhu, Beijing (CN); Chao Jin, Beijing (CN); Tianming Huang, Beijing (CN); Yanlong Kong, Beijing (CN); Yuran Zhang, Beijing (CN)

(73) Assignees: INSTITUTE OF GEOLOGY AND GEOPHYSICS, CAS, Beijing (CN); Yunnan Dianzhong Water Diversion Engineering Co., Kunming (CN)

( * ) Notice: Subject to any disclaimer, the term of this patent is extended or adjusted under 35 U.S.C. 154(b) by 0 days.

(21) Appl. No.: 18/817,347

(22) Filed: Aug. 28, 2024

(51) Int. Cl.
 *G01N 3/04* (2006.01)
 *G01N 3/08* (2006.01)
 *G01N 33/24* (2006.01)

(52) U.S. Cl.
 CPC .............. *G01N 3/04* (2013.01); *G01N 3/08* (2013.01); *G01N 33/24* (2013.01);
 (Continued)

(58) Field of Classification Search
 CPC ............ G01N 3/04; G01N 3/08; G01N 33/24; G01N 2203/0452; G01N 2203/0423; G01N 2203/0429; G01N 2203/0017
 See application file for complete search history.

(56) References Cited

FOREIGN PATENT DOCUMENTS

| CN | 106053209 A | * 10/2016 | ............... G01N 3/02 |
| CN | 110542610 A | 12/2019 | |

(Continued)

OTHER PUBLICATIONS

Chinese Office Action dated Jun. 22, 2024 for Chinese application No. 202410649837.2.

*Primary Examiner* — Jonathan M Dunlap
(74) *Attorney, Agent, or Firm* — Eschweiler & Potashnik, LLC; Nathan T. Lewis

(57) ABSTRACT

A sample mounting device for direct tensile test of rock mass is provided, which includes a first positioning stage, a second positioning stage, a first support piece, a second support piece, and a screw drive mechanism. The second positioning stage is arranged above the first positioning stage and capable of moving up and down, and cushion blocks for gluing with the rock mass are coaxially and detachably arranged at opposite ends of the first positioning stage and the second positioning stage, and a rock mass mounting area is formed between the two cushion blocks. A screw of the screw drive mechanism includes a first thread segment and a second thread segment with opposite thread directions. The first support piece is connected with the first thread segment through a nut seat, and the second support piece is connected with the second thread segment through a nut seat.

10 Claims, 5 Drawing Sheets

(52) U.S. Cl.
CPC ............ *G01N 2203/0017* (2013.01); *G01N 2203/0423* (2013.01); *G01N 2203/0429* (2013.01); *G01N 2203/0452* (2013.01)

(56) References Cited

FOREIGN PATENT DOCUMENTS

| | | | | |
|---|---|---|---|---|
| CN | 110658072 | A | * | 1/2020 |
| CN | 113029768 | A | * | 6/2021 ............ G01N 3/04 |
| CN | 115046852 | A | * | 9/2022 |

* cited by examiner

SAMPLE MOUNTING DEVICE FOR A DIRECT TENSILE TEST OF ROCK MASS

CROSS-REFERENCE TO RELATED APPLICATION

This patent application claims the benefit and priority of Chinese Patent Application No. 2024106498372 filed with the China National Intellectual Property Administration on May 24, 2024, the disclosure of which is incorporated by reference herein in its entirety as part of the present application.

TECHNICAL FIELD

The present disclosure relates to the technical field of a geomechanical test of rock mass engineering, and in particular to a sample mounting device for a direct tensile test of rock mass.

BACKGROUND

With the emergence of a large amount of deep underground engineering, especially in large-scale underground engineering, such as hot dry rock development, nuclear waste geological disposal, underground space infrastructure construction and other underground engineering, tensile failure is easy to occur, which causes a serious security threat. Therefore, it is of great significance to study the tensile strength of various types of rock mass for deep space development. In order to obtain the tensile strength of rock mass, a direct tensile test was mainly carried out in the early development of rock mechanics to determine the tensile strength of rock mass.

However, in the direct tensile test, the rock mass needs to be directly clamped by the gripper of the tensile machine, and force is directly applied to the rock mass in a radial direction, which will easily cause damage to the rock mass and affect the accuracy of the tensile test. In order to solve such a technical problem, the clamping method is often replaced in the prior art. Specifically, it is necessary to glue hard cushion blocks on both sides of the rock mass to be tensioned, and the diameter of the cushion blocks is not less than the diameter of the rock mass. The cushion blocks instead of the rock mass, are clamped by the gripper of the tensile machine, and the cushion blocks and the rock mass are collectively called a tensile sample. However, there are errors in the obtained tensile strength, which is mainly due to the difficulty in achieving complete centering and alignment of the rock mass and the cushion blocks in the tensile test and the difficulty in obtaining accurate tensile strength.

Therefore, there is an urgent need to develop a sample mounting device for direct tensile test of rock mass which can improve the accuracy of the test.

SUMMARY

The purpose of the present disclosure is to provide a sample mounting device for direct tensile test of rock mass to solve the problems in the prior art. The centering and alignment of the rock mass and the cushion blocks are achieved through the cooperation of the coaxially arranged cushion blocks, the first support piece and the second support piece, so as to improve the accuracy of the test.

In order to achieve the above purpose, the present disclosure provides the following solution: a sample mounting device for direct tensile test of rock mass, including a first positioning stage, a second positioning stage, a first support piece, a second support piece, and a screw drive mechanism. The second positioning stage is arranged above the first positioning stage and capable of moving up and down, and cushion blocks for gluing with the rock mass are coaxially and detachably arranged at opposite ends of the first positioning stage and the second positioning stage. A rock mass mounting area is formed between the cushion block of the first positioning stage and the cushion block of the second positioning stage.

A screw of the screw drive mechanism includes a first thread segment and a second thread segment with opposite thread directions. The first support piece is connected with the first thread segment through a nut seat, and the second support piece is connected with the second thread segment through a nut seat. Support end surfaces of the first support piece and the second support piece are opposite to each other, and the first support piece and the second support piece are symmetrically arranged on both sides of the rock mass mounting area.

Preferably, each of the first support piece and the second support piece includes an upright post, and a support plate. One end of the upright post is fixedly connected with the nut seat, and another end of the upright post is connected with the support plate. A support end surface of the support plate is V-shaped.

Preferably, the screw of the screw drive mechanism further includes glue blocking mechanisms. Each glue blocking mechanism is arranged on a corresponding upright post. Each glue blocking mechanism includes a fixed cylinder, a telescopic rod, a semicircular positioning plate, and a semicircular rubber sleeve. An outer diameter of the telescopic rod is in fit with an inner diameter of the fixed cylinder. One end of the telescopic rod is slidably arranged in the fixed cylinder, and another end of the telescopic rod is fixedly connected with the semicircular positioning plate. The semicircular rubber sleeve is connected to a top of the semicircular positioning plate. One end, away from the telescopic rod, of the fixed cylinder is fixedly connected with the upright post. The glue blocking mechanisms are symmetrically arranged on the upright posts. Two semicircular positioning plates are jointed to form a cylindrical barrel in fit with at least one of the cushion blocks. The two semicircular rubber sleeves are jointed to form a glue blocking barrel. The glue blocking barrel is formed with an inverted frustum-shaped cavity, a small-diameter end of the inverted frustum-shaped cavity is flush with a glued surface of the cushion block, and a diameter of the small-diameter end of the inverted frustum-shaped cavity is in fit with a diameter of the cushion block.

Preferably, each support plate is connected with a side wall of the corresponding upright post through an elastic mechanism, and the elastic mechanism comprises a guide cylinder, a connecting rod, and a spring. The connecting rod is slidably arranged in the guide cylinder in an axial direction, and one end, away from the connecting rod, of the guide cylinder is fixedly connected with the upright post. One end, away from the guide cylinder, of the connecting rod is fixedly connected with the support plate, and the spring is arranged between the connecting rod and an inner bottom wall of the guide cylinder.

Preferably, a pitch of the first thread segment and the second thread segment close to a middle of the screw is less than a pitch of the first thread segment and the second thread segment close to ends of the screw.

Preferably, the sample mounting device for direct tensile test of rock mass further includes an operating table. The screw drive mechanism is horizontally arranged on the operating table, and the first positioning stage is fixedly arranged on the operating table corresponding to the middle of the screw. The second positioning stage is arranged in a positioning cylinder and capable of sliding up and down. The positioning cylinder is fixedly arranged on the operating table through a support, and an adjusting mechanism for adjusting a position of the second positioning stage is arranged on the positioning cylinder.

Preferably, the adjusting mechanism includes an adjusting handwheel and a screw. A threaded hole is formed in a top of the positioning cylinder and vertically penetrates through the positioning cylinder, the screw is in threaded connection with the threaded hole, a bottom of the screw is rotatably connected with the second positioning stage, and a top of the screw is in drive connection with the adjusting handwheel.

Preferably, leveling legs are arranged at four corners of a bottom of the operating table.

Preferably, a pressure sensor for detecting a pressure of the rock mass supported is arranged on the support end surface of the first support piece or the second support piece. The pressure sensor is electrically connected with a control system, and the control system is electrically connected with an audible and visual alarm.

Preferably, a lifter is arranged on the nut seat. A lifting end of the lifter is fixedly connected with the first support piece or the second support piece, and a fixed end of the lifter is fixedly connected with the nut seat.

Compared with the prior art, the present disclosure has achieved the following technical effects:

By positioning the upper and lower cushion blocks through the first positioning stage and the second positioning stage, the two cushion blocks are axially aligned, and on this basis, the first support piece and the second support piece are driven by a screw with two opposite thread segments to synchronously move in opposite directions, thus the rock mass is stably supported between the two cushion blocks. The first support piece and the second support piece, which are symmetrically arranged on both sides of the rock mass mounting area, can move synchronously, that is, the rock mass is just located in the rock mass mounting area when supported, so the centering and alignment of the rock mass and the cushion blocks are achieved, thus conducive to improving the accuracy of the subsequent tensile test.

Compared with the prior art, other solutions of the present disclosure have achieved the following technical effects:

The glue blocking mechanism can avoid the loss of a large amount of glue during the initial placement of the rock mass. After the rock mass is supported, the glue stored in the inverted frustum-shaped cavity is filled between the rock mass and the cushion blocks, which can improve the uniformity of the glue layer and further improves the accuracy of the subsequent tensile test.

The spring is arranged to ensure that the spring reacts on the upright post and the nut seat while providing the support effect, such that the threads of the nut seat can be closely attached to the threads of the screw, thus eliminating the influence of the thread clearance on the support effect.

The pressure sensor can detect the support pressure in real time, thus avoiding the problem of rock mass damage caused by excessive pressure.

BRIEF DESCRIPTION OF THE DRAWINGS

To describe the technical solutions of the embodiments of the present disclosure or in the prior art more clearly, the following briefly introduces the accompanying drawings required and used in the embodiments. Apparently, the accompanying drawings in the following description show merely some embodiments of the present disclosure, and for those skilled in the art, other drawings may be obtained according to these accompanying drawings without creative efforts.

Figure 1:
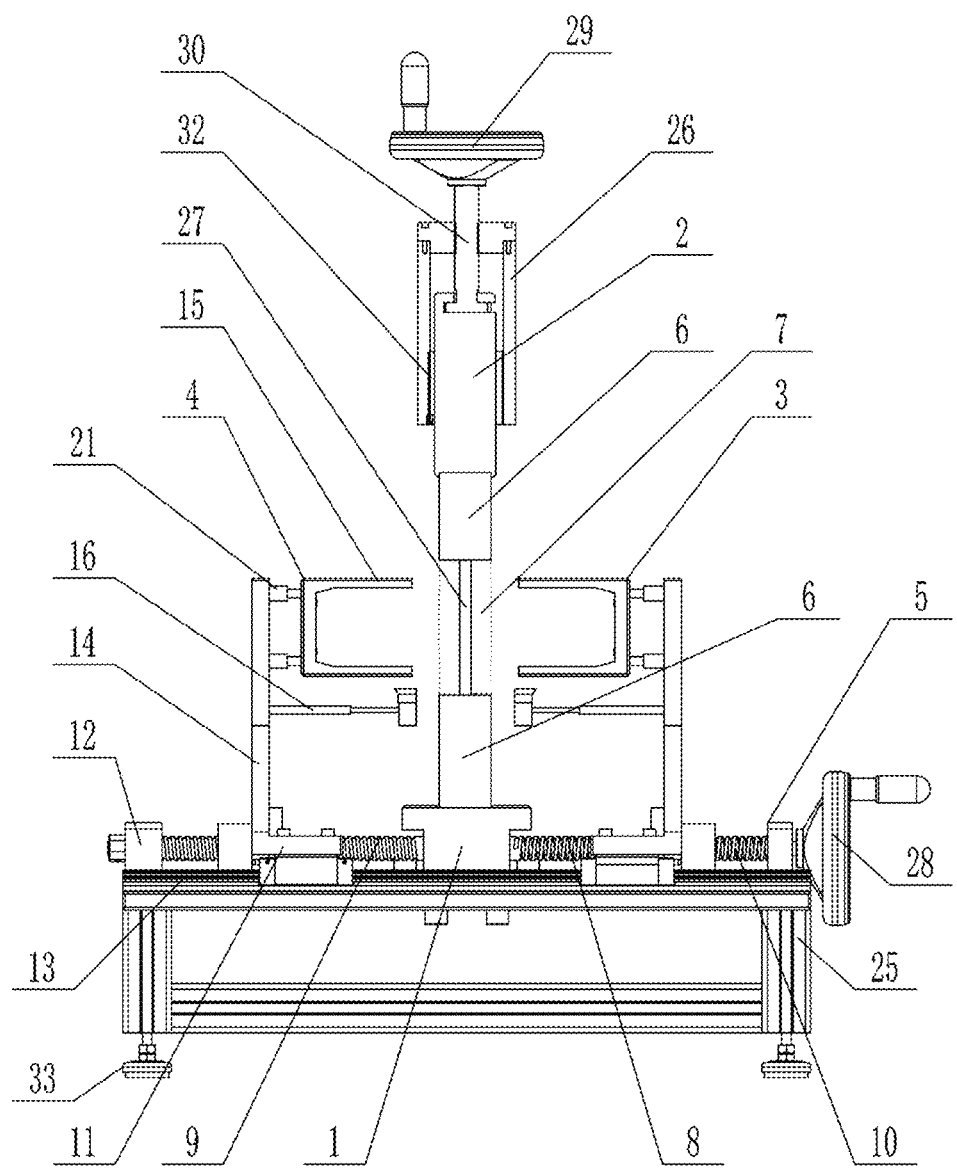
FIG. 1 is a front view of a sample mounting device for direct tensile test of rock mass according to Embodiment 1 of the present disclosure (with a cross-sectional view displayed at a second positioning stage)
Figure 2:
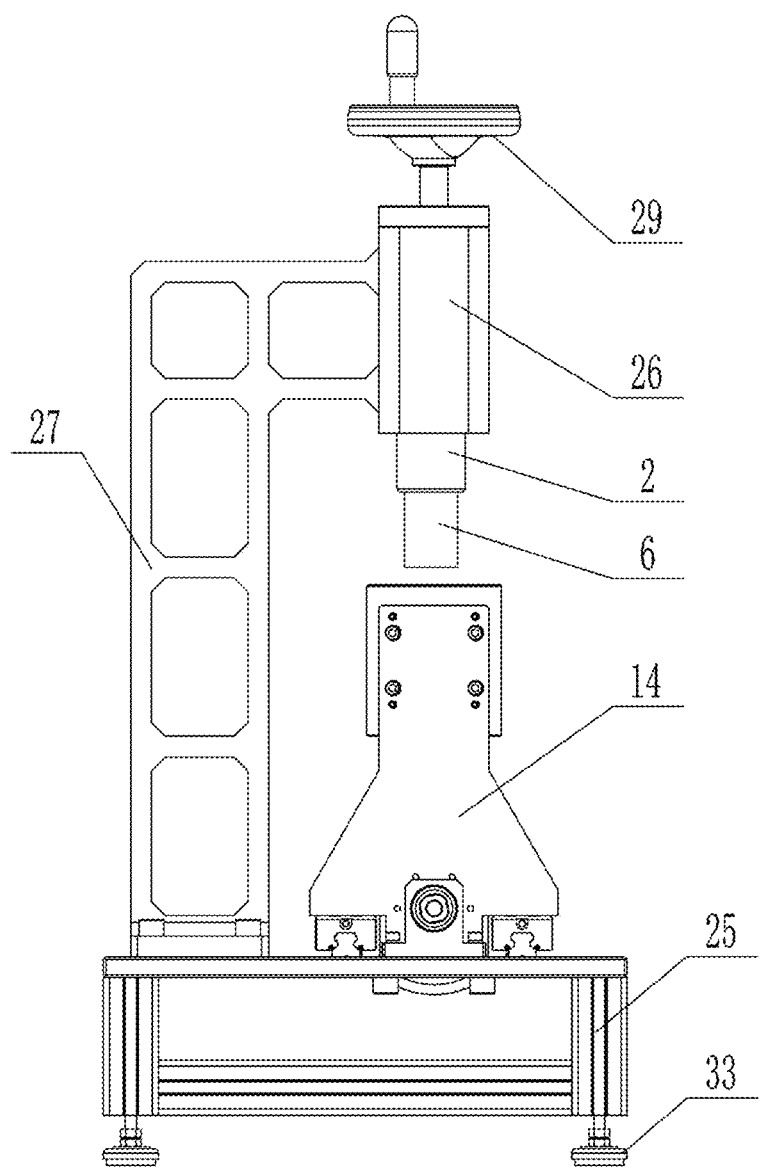
FIG. 2 is a left view of a sample mounting device for direct tensile test of rock mass according to Embodiment 1 of the present disclosure.
Figure 3:
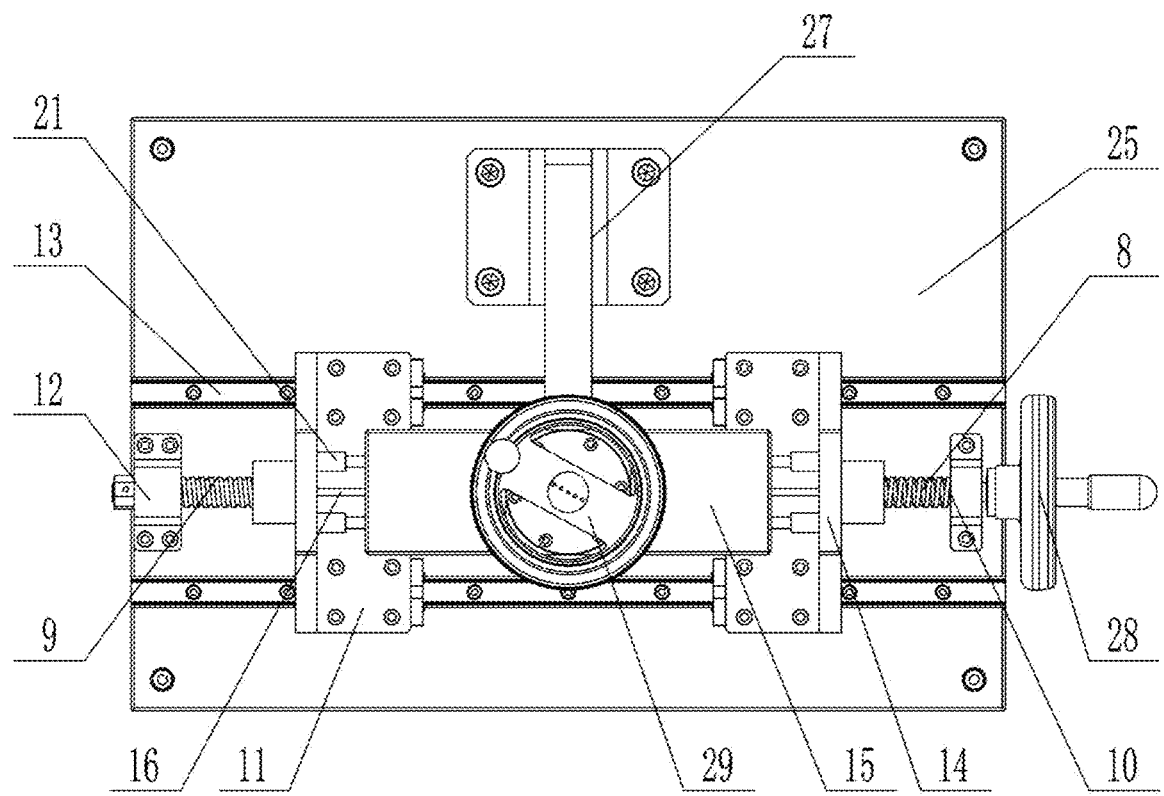
FIG. 3 is a top view of a sample mounting device for direct tensile test of rock mass according to Embodiment 1 of the present disclosure.
Figure 4:
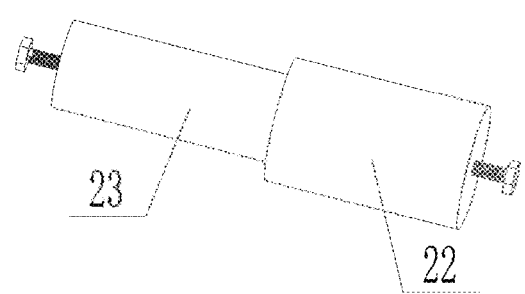
FIG. 4 is a structural schematic diagram of an elastic mechanism according to the present disclosure.
Figure 5:
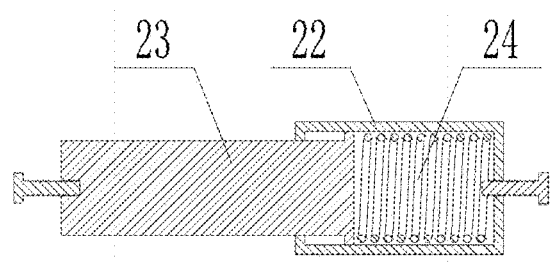
FIG. 5 is a cross-sectional view of an elastic mechanism according to the present disclosure.
Figure 6:
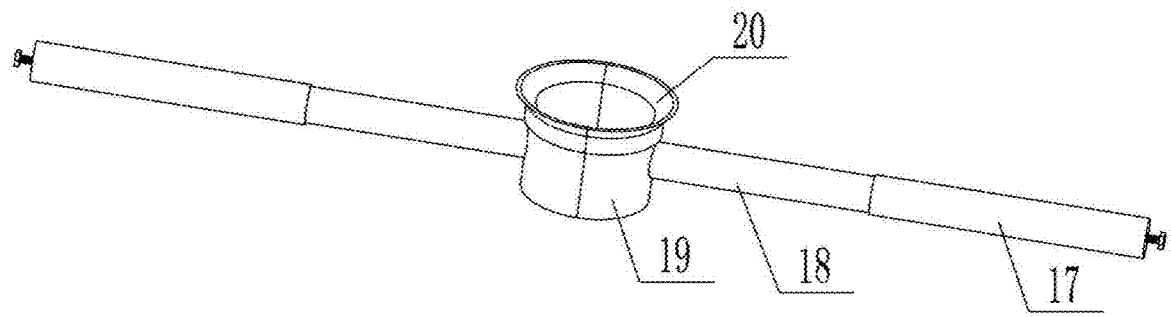
FIG. 6 is a structural schematic diagram of a glue blocking mechanism according to the present disclosure.
Figure 7:
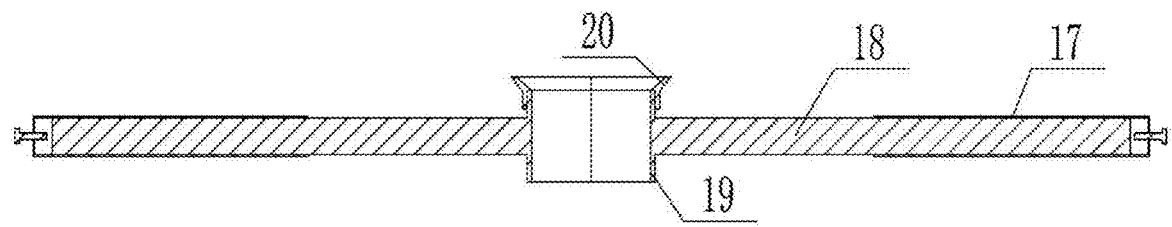
FIG. 7 is a cross-sectional view of a glue blocking mechanism according to the present disclosure.
Figure 8:
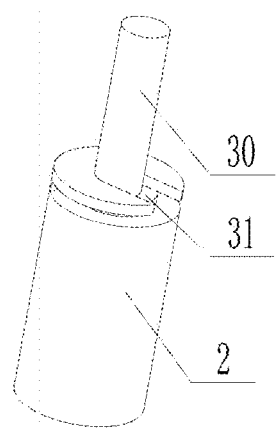
FIG. 8 is a structural schematic diagram of a connection between a screw and a second positioning stage according to the present disclosure.

Reference signs: 1, first positioning stage: 2, second positioning stage: 3, first support piece: 4, second support piece: 5, screw drive mechanism: 6, cushion block: 7, rock mass mounting area: 8, first thread segment: 9, second thread segment: 10, screw: 11, nut seat: 12, bearing housing: 13, slide rail: 14, upright post: 15, support plate: 16, glue blocking mechanism: 17, fixed cylinder: 18, telescopic rod: 19, semicircular positioning plate: 20, semicircular rubber sleeve: 21, elastic mechanism: 22, guide cylinder: 23, connecting rod: 24, spring: 25, operating table: 26, positioning cylinder: 27, support: 28, driving equipment: 29, adjusting handwheel: 30, screw: 31, annular retaining ring: 32, self-lubricating guide sleeve: 33, leveling leg: 34, lifter.

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. Based on the embodiments of the present disclosure, all other embodiments obtained by those skilled in the art without creative efforts shall fall within the protection scope of the present disclosure.

The purpose of the present disclosure is to provide a sample mounting device for direct tensile test of rock mass to solve the problems in the prior art. The centering and alignment of the rock mass and the cushion block are achieved through the cooperation of the coaxially arranged cushion blocks, the first support piece, and the second support piece, so as to improve the accuracy of the test.

In order to make the above purpose, features and advantages of the present disclosure more apparent and easy to understand, the present disclosure is further described in detail below with reference to the accompanying drawings and embodiments.

As shown in FIGS. 1 to 8, a sample mounting device for direct tensile test of rock mass is provided, which includes a first positioning stage 1, a second positioning stage 2, a first support piece 3, a second support piece 4, and a screw drive mechanism 5. The second positioning stage 2 is arranged above the first positioning stage 1 and capable of moving up and down through an adjusting mechanism, and cushion blocks 6 for gluing with the rock mass are coaxially and detachably arranged at opposite ends of the first positioning stage 1 and the second positioning stage 2. A diameter of the cushion blocks 6 is not less than that of the rock mass. Specifically, opposite surfaces of the first positioning stage 1 and the second positioning stage 2 are formed with grooves in fit with the cushion blocks 6, and the cushion blocks 6 are inserted into the grooves. By increasing the friction force between the grooves and the cushion blocks 6, it is ensured that the upper cushion block 6 will not detach from the groove under the influence of the gravity. The rock mass mounting area 7 is formed between the cushion block 6 of the first positioning stage 1 and the cushion block 6 of the second positioning stage 2. The upper and lower cushion blocks 6 are positioned through the second positioning stage 2 and the first positioning stage 1, respectively, making the two cushion blocks 6 coaxially aligned.

The screw 10 of the screw drive mechanism 5 includes a first screw segment 8 and a second screw segment 9 with opposite thread directions. The first support piece 3 is connected with the first screw segment 8 through the nut seat 11, and the second support piece 4 is connected with the second screw segment 9 through the nut seat 11. Support end surfaces of the first support piece 3 and the second support piece 4 are opposite to each other. The first support piece 3 and the second support piece 4 are symmetrically arranged on both sides of the rock mass mounting area 7. The first support piece 3 and the second support piece 4 are driven through the screw 10 with two opposite thread segments to synchronously move in opposite directions, thus stably support the rock mass between the two cushion blocks 6 in a clamping manner. As the first support piece 3 and the second support piece 4 are symmetrically arranged and move synchronously, the rock mass is just located in the rock mass mounting area 7 when being supported, achieving the centering and alignment of the rock mass and the cushion blocks 6, and conducive to improving the accuracy of the subsequent tensile test.

Each of the first support piece 3 and the second support piece 4 includes an upright post 14, and a support plate 15. The support plate 15 is horizontally arranged, and an end surface, close to the rock mass mounting area 7, of the support plate 15 is the support end surface. One end of the upright post 14 is fixedly connected with the nut seat 11 by a bolt, and another end of the upright post 14 is connected with the support plate 15 by a bolt. Compared with welding, the bolt connection method can improve the convenience of assembling and disassembling. In order to improve the clamping and support effect on the rock mass, the support end surface of the support plate 15 is V-shaped.

The upright post 14 may be of a cylindrical structure, or a plate-shaped structure, and so on.

Multiple support plates 15 are arranged on the single upright post 14, and the multiple support plates are arranged at intervals from top to bottom, so as to improve the contact area with the rock mass and reduce damage to the rock mass caused by stress concentration.

The multiple support plates 15 can be jointly welded or bolted to a vertically arranged connection plate to form a module, and the connection plate is further connected with the upright post 14 by a bolt.

Since the rock mass may be with a certain inclination during initial placement of the rock mass, glue between the rock mass and the cushion block 6 is partly squeezed out when the rock mass is pressed against the lower cushion block 6, such that an upper surface of the whole glue layer is inclined. Therefore, during the rock mass is supported, there may be a movement state in which the lower end of an originally inclined bottom of the rock mass is lifted upward and the higher end of the originally inclined bottom of the rock mass is pressed downward. In such a movement state, a glue-free area is formed at the lower end that is lifted upward, and the glue below the higher end that is pressed downward cannot be filled into the glue-free area completely, which affects the uniformity of glue distribution between the cushion blocks 6 and the rock mass, and further affects the accuracy of the subsequent tensile test. Therefore, each glue blocking mechanism 16 is arranged on a corresponding upright post 14. The glue blocking mechanism 16 includes a fixed cylinder 17, a telescopic rod 18, a semicircular positioning plate 19, and a semicircular rubber sleeve 20. Both the semicircular positioning plate 19 and the semicircular rubber sleeve 20 are made of materials that are not easily bonded to epoxy resin. For example, the semicircular rubber sleeve 20 is made of silicone rubber, and the semicircular positioning plate 19 is made of polyethylene, polytetrafluoroethylene, etc. An outer diameter of the telescopic rod 18 is in fit with an inner diameter of the fixed cylinder 17. One end of the telescopic rod 18 is slidably arranged in the fixed cylinder 17, and the other end of the telescopic rod 18 is fixedly connected with the semicircular positioning plate 19. The fixed cylinder 17 is fixedly connected with the upright post 14 by a bolt, and the semicircular rubber sleeve 20 is connected to or integrally formed on the top of the semicircular positioning plate 19. One end, away from the telescopic rod 18, of the fixed cylinder 17 is fixedly connected with the upright post 14, the glue blocking mechanisms 16 are symmetrically arranged on the two upright posts 14, the two semicircular positioning plates 19 are jointed to form a cylindrical barrel in fit with the cushion block 6, and the two semicircular rubber sleeves 20 are jointed to form a glue blocking barrel with an inverted frustum-shaped cavity. A small-diameter end of the inverted frustum-shaped cavity is flush with a glued surface of the cushion block 6, and a diameter of the small-diameter end of the inverted frustum-shaped cavity is in fit with that of the cushion block 6. The working principle is as follows: before support, the telescopic rods 18 on both sides are controlled to extend to make two semicircular positioning plates 19 jointed on a peripheral side of the cushion block 6. In this case, the inverted frustum-shaped cavity is located on an upper surface of the cushion block 6, and then glue is coated on the cushion block 6. In the process of placing the rock mass after finishing coating, due to the block of the inverted frustum-shaped cavity, the squeezed glue remains at the bottom of the inverted frustum-shaped cavity instead of losing, such that when a glue-free area is formed in the subsequent support process, the remained glue can be filled into the glue-free area, thus improving the uniformity of the glue layer and improving the accuracy of the subsequent tensile test. As the fixed cylinder 17 and the telescopic rod 18 are formed as a freely telescoping structure, a jointing state of the two semicircular positioning plates 19 cannot be affected during the support movement.

The support plate 15 is connected with a side wall of the upright post 14 through an elastic mechanism 21. The elastic mechanism 21 includes a guide cylinder 22, a connecting rod 23, and a spring 24. The connecting rod 23 is slidably arranged in the guide cylinder 22 in the axial direction, and one end, away from the connecting rod 23, of the guide cylinder 22 is fixedly connected with the upright post 14 by a bolt. One end, away from the guide cylinder 22, of the connecting rod 23 is fixedly connected with the support plate 15 by a bolt, and a spring 24 is arranged between the connecting rod 23 and an inner bottom wall of the guide cylinder 22. Without support, the spring 24 is in a normal state. The spring 24 is provided to ensure that the spring react on the upright post 14 and the nut seat 11 while providing the support effect, such that the threads of the nut seat 11 can be closely attached to the threads of the screw 10, thus eliminating the influence of the thread clearance on the support effect.

In order to prevent the connecting rod 23 from falling out from the guide cylinder 22, annular flanges can be arranged at a port of the guide cylinder 22, close to the connecting rod 23 and at a portion of the connecting rod 23, located in the guide cylinder 22. The annular flange of the guide cylinder 22 is located on a movement path of the annular flange of the connecting rod 23 to block the connecting rod 23 and prevent it from falling off. After the annular flanges are arranged, the annular flange of the connecting rod 23 needs to fit with the inner diameter of the guide cylinder 22.

On the basis of providing multiple support plates 15, the connection plate connected with the multiple support plates 15 is threaded with an end of the connecting rod 23, and multiple elastic mechanisms can be arranged between the connecting rod and the upright post 14.

In a method of making a pitch of the first thread segment 8 and the second thread segment 9 close to a middle of the screw 10 less than a pitch of the first thread segment 8 and the second thread segment 9 close to ends of the screw 10, the movement speed at the initial stage of the support movement can be improved, which is helpful to save time and improve efficiency. The change of pitch is gradual, that is, the pitch decreases gradually from the end to the middle.

The sample mounting device for a direct tensile test of rock mass further includes an operating table 25. The screw drive mechanism 5 is horizontally arranged on the operating table 25, and the first positioning stage 1 is fixedly arranged on the operating table 25, and arranged corresponding to the middle of the screw 10. The second positioning stage 2 is arranged in the positioning cylinder 26 and capable of sliding up and down. The positioning cylinder 26 is fixedly arranged on the operating table 25 through a support 27, and an adjusting mechanism for adjusting a position of the second positioning stage 2 is arranged on the positioning cylinder 26.

The screw drive mechanism 5 includes a screw 10, a nut seat 11, a bearing housing 12, and a driving equipment 28. The screw 10 is arranged on the operating table 25 through the bearing housing 12, the nut seat 11 is threaded with the screw 10, and the driving equipment 28 is in drive connection with the screw 10. In order to save the cost, the driving equipment 28 may be selected as a handwheel.

A hole for avoiding the screw 10 is arranged at the bottom of the first positioning stage 1, and through the hole, the first positioning stage is directly buckled to the middle of the screw 10.

A slide rail 13 for guiding the movement of the nut seat 11 is arranged on the operating table 25, and a chute is correspondingly arranged on the nut seat 11.

The adjusting mechanism for adjusting the position of the second positioning stage 2 includes an adjusting handwheel 29, and a screw 30. A threaded hole is formed in a top of the positioning cylinder 26 and vertically penetrates through the positioning cylinder 26. The screw 30 is in threaded connection with the threaded hole, the bottom of the screw 30 is rotatably connected with the second positioning stage, and the top of the screw 30 is in drive connection with the adjusting handwheel 29.

A method of rotary connection between the screw 30 and the second positioning stage 2 may be as follows: a bearing is arranged on the top of the second positioning stage 2 which is rotatably connected with the screw 30 through the bearing. Alternatively, an annular retaining ring 31 is fixedly arranged at the bottom of the screw 30, and a groove is formed in a side wall of the second positioning stage 2. The groove penetrates through the top of the second positioning stage 2 upwards, and the bottom of the groove is expanded to form a space for accommodating the annular retaining ring 31. A width of a notch, corresponding to the top of the second positioning stage 2, of the groove is greater than a diameter of the screw 30 and smaller than an outer diameter of the annular retaining ring 31, such that the second positioning stage 2 can be hung on the screw 30 by hanging. In order to prevent the screw 30 from driving the second positioning stage 2 to rotate synchronously through the annular retaining ring 31 to affect the uniformity of glue pressing, a vertical strip protrusion can be arranged on a peripheral wall of the second positioning stage 2, and a vertical strip slot can be arranged on the positioning cylinder 26, and the strip protrusion is arranged in the strip slot and capable of sliding up and down to limit the rotation of the strip slot.

A cover is detachably arranged at the top of the positioning cylinder 26. Specifically, the cover at the top is connected with the barrel of the positioning cylinder 26 by a bolt, thus facilitating the mounting of the second positioning stage 2 and the screw 30.

A self-lubricating guide sleeve 32 is arranged on an inner wall of the positioning cylinder 26 to reduce the friction force between the positioning cylinder 26 and the second positioning stage 2.

Leveling legs 33 are arranged at four corners of a bottom of the operating table 25. The leveling legs 33 can employ bolt legs, and levelness of the whole operating table 25 can be adjusted by screwing the bolt let at each corner.

A pressure sensor is arranged on the support end surface of the first support piece 3 or the second support piece 4 to detect pressure when the rock mass is supported. The pressure sensor is electrically connected with a control system, and the control system is electrically connected with an audible and visual alarm. When the pressure is large, the audible and visual alarm gives an alarm to avoid crushing damage to the rock mass.

During actual application, cushion blocks 6 are mounted on the first positioning stage 1 and the second positioning stage 2, and glue is coated on the cushion block 6 of the first positioning stage 1, then the rock mass is placed on the cushion block 6 of the first positioning stage 1, the screw 10 is driven to rotate through the handwheel, and the nut seat 11 moves synchronously to drive the first support piece 3 and the second support piece 4 to clamp and support the rock mass, and the glue is coated on the top of the rock mass or the cushion block 6 of the second positioning stage 2 after the support is completed. The adjusting handwheel 29 is turned to control the second positioning stage 2 to move downwards till to form a connecting glue layer with the rock mass. Finally, after the glue solidifies, the adjusting handwheel 29 is turned to control the second positioning stage 2 to move upwards, and the handwheel is turned to control the first support piece 3 and the second support piece 4 to move reversely, thus pulling out the rock mass connected with the cushion block 6 from the first positioning stage 1.

Embodiment 2

Figure 9:
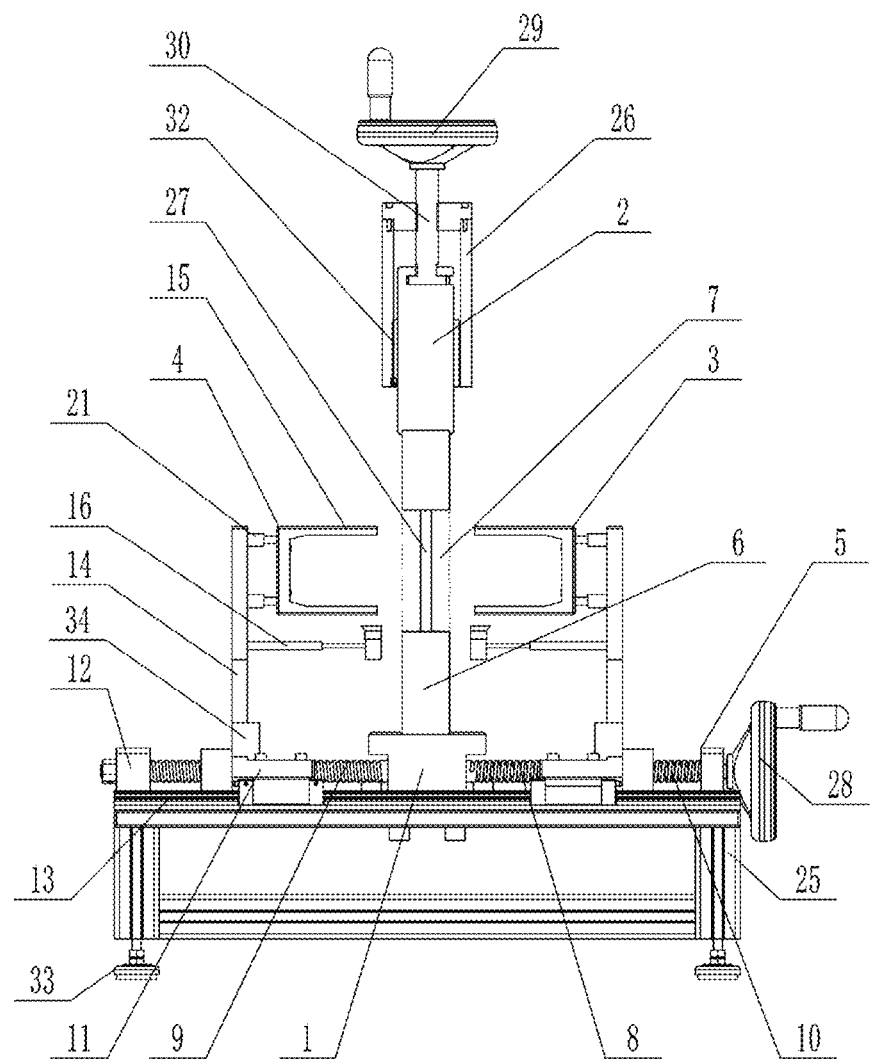
FIG. 9 is a front view of a sample mounting device for direct tensile test of rock mass according to Embodiment 2 of the present disclosure (with a cross-sectional view displayed at a second positioning stage).

As shown in FIG. 9, a difference between Embodiment 2 and Embodiment 1 is that the lifter 34 is arranged on the nut seat 11, and the lifter may employ an electric lifter. A lifting end of the lifter 34 is fixedly connected with the first support piece 3 or the second support piece 4, and a fixed end is fixedly connected with the nut seat 11. After the rock mass is clamped by the first support piece 3 and the second support piece 4, the lifter 34 can control a distance between the rock mass and the cushion block 6 on the first positioning stage 1 through the lifting movement, while a distance between the cushion block 6 on the second positioning stage 2 and the rock mass can be controlled through the adjusting handwheel 29, thus controlling the thickness of the glue layer on both sides of the rock mass.

Adaptive changes made according to actual needs are within the scope of protection of the present disclosure.

It should be noted that it is apparent to those skilled in the art that the present disclosure is not limited to the details of the above exemplary embodiments, and can be realized in other specific forms without departing from the spirit or basic characteristics of the present disclosure. Therefore, the embodiments should be considered as exemplary and non-limiting in all aspects, and the scope of the present disclosure is defined by the appended claims rather than the above description. So it is intended that all changes that fall within the meaning and range of equivalents of the claims are included in the present disclosure. Any reference signs in the claims should not be regarded as limiting the claims involved.

Specific examples are used in the present disclosure for description of the principles and embodiments of the present disclosure. The description of the above embodiments is merely used to help illustrate the method and its core principles of the present disclosure. Meanwhile, those skilled in the art can make various modifications in terms of specific embodiments and scope of application in accordance with the teachings of the present disclosure. In conclusion, the content of this specification shall not be construed as a limitation to the present disclosure.

What is claimed is:

1. A sample mounting device for direct tensile test of rock mass, wherein the sample mounting device comprises
    a first positioning stage, a second positioning stage, a first support piece, a second support piece, and a screw drive mechanism;
    the second positioning stage is arranged above the first positioning stage and capable of moving up and down, cushion blocks for gluing with the rock mass are coaxially and detachably arranged at opposite ends of the first positioning stage and the second positioning stage, and a rock mass mounting area is formed between the cushion block of the first positioning stage and the cushion block of the second positioning stage;
    a screw of the screw drive mechanism comprises a first thread segment and a second thread segment with opposite thread directions, the first support piece is connected with the first thread segment through a nut seat, the second support piece is connected with the second thread segment through a nut seat, support end surfaces of the first support piece and the second support piece are opposite to each other, and the first support piece and the second support piece are symmetrically arranged on both sides of the rock mass mounting area.

2. The sample mounting device for direct tensile test of rock mass according to claim 1, wherein each of the first support piece and the second support piece comprises an upright post, and a support plate, one end of the upright post is fixedly connected with the nut seat, and an other end of the upright post is connected with the support plate; and
    a support end surface of the support plate is V-shaped.

3. The sample mounting device for direct tensile test of rock mass according to claim 2, further comprising glue blocking mechanisms, wherein each glue blocking mechanism is arranged on a corresponding upright post;
    each glue blocking mechanism comprises a fixed cylinder, a telescopic rod, a semicircular positioning plate, and a semicircular rubber sleeve;
    an outer diameter of the telescopic rod is in fit with an inner diameter of the fixed cylinder;
    one end of the telescopic rod is slidably arranged in the fixed cylinder, and another end of the telescopic rod is fixedly connected with the semicircular positioning plate;
    the semicircular rubber sleeve is connected to a top of the semicircular positioning plate;
    one end, away from the telescopic rod, of the fixed cylinder is fixedly connected with the upright post;
    the glue blocking mechanisms are symmetrically arranged on the upright posts;
    two semicircular positioning plates are jointed to form a cylindrical barrel in fit with at least one of the cushion blocks;
    the two semicircular rubber sleeves are jointed to form a glue blocking barrel; the glue blocking barrel is formed with an inverted frustum-shaped cavity, a small-diameter end of the inverted frustum-shaped cavity is flush with a gluing surface of the cushion block, and a diameter of the small-diameter end of the inverted frustum-shaped cavity is in fit with a diameter of the cushion block.

4. The sample mounting device for direct tensile test of rock mass according to claim 2, wherein each support plate is connected with a side wall of the corresponding upright post through an elastic mechanism, the elastic mechanism comprises a guide cylinder, a connecting rod, and a spring;
    the connecting rod is slidably arranged in the guide cylinder in an axial direction, and one end, away from the connecting rod, of the guide cylinder is fixedly connected with the upright post;
    one end, away from the guide cylinder, of the connecting rod is fixedly connected with the support plate, and the spring is arranged between the connecting rod and an inner bottom wall of the guide cylinder.

5. The sample mounting device for direct tensile test of rock mass according to claim 1, wherein a pitch of the first thread segment and the second thread segment close to a middle of the screw is less than a pitch of the first thread segment and the second thread segment close to ends of the screw.

6. The sample mounting device for direct tensile test of rock mass according to claim 1, further comprising an operating table, wherein the screw drive mechanism is horizontally arranged on the operating table, and the first positioning stage is fixedly arranged on the operating table corresponding to the middle of the screw;

the second positioning stage is arranged in a positioning cylinder and capable of sliding up and down; the positioning cylinder is fixedly arranged on the operating table through a support, and an adjusting mechanism for adjusting a position of the second positioning stage is arranged on the positioning cylinder.

7. The sample mounting device for direct tensile test of rock mass according to claim 6, wherein the adjusting mechanism comprises an adjusting handwheel, and a screw;

a threaded hole is formed in a top of the positioning cylinder and vertically penetrates through the positioning cylinder, the screw is in threaded connection with the threaded hole, a bottom of the screw is rotatably connected with the second positioning stage, and a top of the screw is in drive connection with the adjusting handwheel.

8. The sample mounting device for direct tensile test of rock mass according to claim 6, wherein leveling legs are arranged at four corners of a bottom of the operating table.

9. The sample mounting device for direct tensile test of rock mass according to claim 1, wherein a pressure sensor for detecting a pressure of the rock mass supported is arranged on the support end surface of the first support piece or the second support piece, and the pressure sensor is electrically connected with a control system, and the control system is electrically connected with an audible and visual alarm.

10. The sample mounting device for direct tensile test of rock mass according to claim 1, wherein a lifter is arranged on the nut seat, a lifting end of the lifter is fixedly connected with the first support piece or the second support piece, and a fixed end of the lifter is fixedly connected with the nut seat.

* * * * *